(12) United States Patent
Berry et al.

(10) Patent No.: US 10,232,157 B2
(45) Date of Patent: Mar. 19, 2019

(54) HOLLOW MICRONEEDLE WITH BEVELED TIP

(71) Applicant: 3M INNOVATIVE PROPERTIES COMPANY, St. Paul, MN (US)

(72) Inventors: Dennis G. Berry, Maplewood, MN (US); Paul A. Martinson, Maplewood, MN (US); Ryan Patrick Simmers, Fargo, ND (US)

(73) Assignee: 3M Innovative Properties Company, St. Paul, MN (US)

( * ) Notice: Subject to any disclaimer, the term of this patent is extended or adjusted under 35 U.S.C. 154(b) by 466 days.

(21) Appl. No.: 14/904,975

(22) PCT Filed: Jul. 10, 2014

(86) PCT No.: PCT/US2014/046099
§ 371 (c)(1),
(2) Date: Jan. 14, 2016

(87) PCT Pub. No.: WO2015/009524
PCT Pub. Date: Jan. 22, 2015

(65) Prior Publication Data
US 2016/0136406 A1    May 19, 2016

Related U.S. Application Data

(60) Provisional application No. 61/846,934, filed on Jul. 16, 2013.

(51) Int. Cl.
*A61M 37/00*     (2006.01)
*A61B 5/15*      (2006.01)
(Continued)

(52) U.S. Cl.
CPC ... *A61M 37/0015* (2013.01); *A61B 5/150022* (2013.01); *A61B 5/150282* (2013.01);
(Continued)

(58) Field of Classification Search
CPC ...... A61M 37/0015; A61M 2037/0023; A61M 2037/003; A61M 2037/0038; A61M 2037/0053; A61M 2037/0061
See application file for complete search history.

(56) References Cited

U.S. PATENT DOCUMENTS 3,308,822 A    3/1967   De Luca
4,490,139 A    12/1984  Huizenga et al.
(Continued)

FOREIGN PATENT DOCUMENTS

CN           101244303 B        9/2010
DE    10 2008 052 749           5/2010
(Continued)

*Primary Examiner* — Nathan R Price
*Assistant Examiner* — Courtney B Fredrickson
(74) *Attorney, Agent, or Firm* — Eric E. Silverman (57) ABSTRACT

An article having at least one microneedle (160, 260) is provided. The microneedle includes a base (162), an elongated body (161) having a central axis (130) and a body diameter (168), a tip portion (166), and a hollow channel (170). The a tip portion includes a tip (164), a first bevel face (140) oriented diagonally with respect to the central axis and extending through at least 75% of the body diameter, a second bevel face (146) oriented substantially perpendicular to the central axis and intersecting the first bevel face, and a bevel opening defined by a first edge (174) of the first bevel face and a second edge (176) of the second bevel face. The hollow channel extends axially into the body from the bevel opening (172).

18 Claims, 6 Drawing Sheets

(51) Int. Cl.
  B29C 45/26      (2006.01)
  B29C 59/02      (2006.01)
  B28B 1/24       (2006.01)
  B29L 31/00          (2006.01)
  B29C 67/24          (2006.01)
  B29C 45/00          (2006.01)
  B29K 69/00          (2006.01)

(52) U.S. Cl.
  CPC .. *A61B 5/150396* (2013.01); *A61B 5/150984* (2013.01); *B28B 1/24* (2013.01); *B29C 45/2626* (2013.01); *B29C 45/2628* (2013.01); *B29C 59/025* (2013.01); *A61M 2037/003* (2013.01); *A61M 2037/0023* (2013.01); *A61M 2037/0053* (2013.01); *A61M 2037/0061* (2013.01); *B29C 67/247* (2013.01); *B29C 2045/0094* (2013.01); *B29C 2059/023* (2013.01); *B29K 2069/00* (2013.01); *B29L 2031/756* (2013.01); *B29L 2031/7544* (2013.01)

(56) References Cited

U.S. PATENT DOCUMENTS

| | | |
|---|---|---|
| 5,575,780 A | 11/1996 | Saito |
| 5,752,942 A | 5/1998 | Doyle et al. |
| 6,091,975 A | 7/2000 | Daddona et al. |
| 6,312,612 B1 | 11/2001 | Sherman et al. |
| 6,379,324 B1 | 4/2002 | Gartstein et al. |
| 6,451,240 B1 | 9/2002 | Sherman et al. |
| 6,471,903 B2 | 10/2002 | Sherman et al. |
| 6,517,523 B1 | 2/2003 | Kaneko et al. |
| 6,558,361 B1 | 5/2003 | Yeshurun |
| 6,824,378 B2 | 11/2004 | King et al. |
| 7,070,583 B1 | 7/2006 | Higuchi et al. |
| 7,648,484 B2 | 1/2010 | Yeshurun et al. |
| 8,088,321 B2 | 1/2012 | Ferguson et al. |
| 8,246,893 B2 | 8/2012 | Ferguson et al. |
| 2003/0009113 A1* | 1/2003 | Olson ............... A61B 5/14532 600/573 |
| 2005/0049549 A1* | 3/2005 | Wong ............... A61B 10/0064 604/46 |
| 2005/0065463 A1 | 3/2005 | Tobinaga et al. |
| 2005/0261631 A1 | 11/2005 | Clarke et al. |
| 2006/0202385 A1* | 9/2006 | Xu ............... A61M 37/0015 264/219 |
| 2007/0078376 A1* | 4/2007 | Smith ............... A61M 37/0015 604/21 |
| 2009/0054842 A1 | 2/2009 | Yeshurun et al. |
| 2009/0099537 A1 | 4/2009 | DeVoe et al. |
| 2010/0193997 A1 | 8/2010 | Frederickson et al. |
| 2010/0305516 A1 | 12/2010 | Xu et al. |
| 2011/0046556 A1 | 2/2011 | Kraft |
| 2011/0172605 A1 | 7/2011 | Berenschot et al. |
| 2011/0172609 A1 | 7/2011 | Moga et al. |
| 2011/0192562 A1 | 8/2011 | Motoi et al. |
| 2011/0213335 A1 | 9/2011 | Burton et al. |
| 2012/0041337 A1 | 2/2012 | Ferguson et al. |
| 2012/0123387 A1 | 5/2012 | Gonzalez et al. |
| 2012/0258284 A1 | 10/2012 | Rendon |
| 2014/0236075 A1 | 8/2014 | Sugimura |

FOREIGN PATENT DOCUMENTS

| | | |
|---|---|---|
| EP | 2 062 611 | 5/2009 |
| WO | WO 2006/025786 | 3/2006 |
| WO | WO 2008/027011 | 3/2008 |
| WO | WO 2009/130926 | 10/2009 |
| WO | WO 2012/074576 | 6/2012 |
| WO | WO 2012/122162 | 9/2012 |
| WO | WO 2012/126784 | 9/2012 |
| WO | WO 2013/061825 | 5/2013 |
| WO | WO 2014/099404 | 6/2014 |
| WO | WO 2014/105458 | 7/2014 |
| WO | WO 2015/009523 | 1/2015 |
| WO | WO 2015/009530 | 1/2015 |
| WO | WO 2015/009531 | 1/2015 |

* cited by examiner

HOLLOW MICRONEEDLE WITH BEVELED TIP

CROSS REFERENCE TO RELATED APPLICATIONS

This application is a national stage filing under 35 U.S.C. 371 of PCT/US2014/046099, filed Jul. 10, 2014, which claims priority to U.S. Provisional Patent Application No. 61/846,934, filed Jul. 16, 2013, the disclosure of which is incorporated by reference in its entirety herein.

BACKGROUND

Transdermal and topical drug delivery can be used for therapeutic treatment, but the number of molecules that can be effectively delivered using these routes can be limited by the barrier properties of skin. The main barrier to transport of molecules through the skin is the stratum corneum (the outermost layer of the skin).

A number of different skin treatment methods have been proposed in order to increase the permeability or porosity of the outermost skin layers, such as the stratum corneum, thus enhancing drug delivery through or into those layers. The stratum corneum is a complex structure of compact keratinized cell remnants separated by lipid domains. The stratum corneum is formed of keratinocytes, which comprise the majority of epidermal cells that lose their nuclei and become corneocytes. These dead cells comprise the stratum corneum, which has a thickness of only about 10-30 microns and protects the body from invasion by exogenous substances and the outward migration of endogenous fluids and dissolved molecules. Various skin treatment methods include the use of microneedles, laser ablation, RF ablation, heat ablation, sonophoresis, iontophoresis, or a combination thereof.

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can sequentially or simultaneously pass through that layer and into the tissues below. Microneedles of these devices pierce the stratum corneum upon contact, making a plurality of microscopic slits which serve as passageways through which molecules of active components can be delivered into the body. In delivering an active component, the microneedle device can be provided with a reservoir for temporarily retaining an active component in liquid form prior to delivering the active component through the stratum corneum. In some constructions, the microneedles can be hollow to provide a liquid flow path directly from the reservoir and through the microneedles to enable delivery of the therapeutic substance through the skin. In alternate constructions, active component(s) may be coated on the microneedle array and delivered directly through the skin after the stratum corneum has been punctured.

Microneedle arrays can be used in conjunction with an applicator device capable of being used several times or as a single-use device. The microneedle arrays are generally used once and then discarded.

SUMMARY

It is now known that the configuration of the tip portion of a hollow microneedle can result in more consistent and effective administration of a composition (e.g., a pharmaceutically-active composition) into skin tissue. Now, it is also known that the configuration of the present disclosure also results in a more robust manufacturing process to make articles with hollow microneedles.

The present disclosure generally relates to articles that comprise at least one hollow microneedle. In particular, the present disclosure relates to the tip portion of the hollow microneedle and the configuration of a bevel and an opening in the bevel proximate the tip of the microneedle Some aspects of the present disclosure provide an article. The article can comprise at least one microneedle. The at least one microneedle can comprise a base, an elongated body having a central axis and a body diameter, a tip portion, and a hollow channel. The tip portion comprises a tip, a first bevel face oriented diagonally with respect to the central axis and extending through about 75% to about 95% of the body diameter, a second bevel face oriented substantially perpendicular to the central axis and intersecting the first bevel face, and a bevel opening defined by a first edge of the first bevel face and a second edge of the second bevel face. The hollow channel extends axially into the body from the bevel opening. The second bevel face extends through no more than about 25% of the body diameter.

Other aspects of the present disclosure provide a method of making an article comprising at least one hollow microneedle. The hollow microneedle comprises a body having a central axis, a body diameter, a base, a tip portion, and a hollow channel. The method can comprise providing a first mold half comprising at least one cavity, wherein the at least one cavity includes a cavity opening and a cavity surface having a first projection extending therefrom toward the cavity opening, wherein the first projection defines a first segment of the hollow channel, the first segment extending into the body of the microneedle from the base, wherein the first projection comprises a first longitudinal axis. The method further can comprise providing a second mold half comprising at least one second projection extending therefrom; wherein the at least one second projection defines a tip portion of the at least one microneedle and a second segment of the hollow channel, the second segment extending into the body of the microneedle from a bevel opening proximate the tip of the at least one microneedle; wherein the at least one second projection comprises a second longitudinal axis; wherein the second projection is shaped and dimensioned to define the tip portion. The method further can comprise contacting at least the first mold half or the second mold half with moldable material, inserting the at least one second projection into the cavity opening so that the first projection is substantially aligned with the second projection, and forming the article. The second projection causes formation of the tip portion of the at least one microneedle to comprise a tip, a first bevel face oriented diagonally with respect to the central axis and extending through about 75% to about 95% of the body diameter, a second bevel face oriented substantially perpendicular to the central axis and intersecting the first bevel face, a bevel opening defined by a first edge of the first bevel face and a second edge of the second bevel face, and a hollow channel that extends axially into the body from the bevel opening. The second projection causes formation of the tip portion of the at least one microneedle such that the second bevel face extends through no more than about 25% of the body diameter.

The phrase "injection apparatus" refers to an integrated device capable of delivering or extracting a fluid over a certain period and is not limited to devices intended solely for an infusion. Accordingly, an injection apparatus may be used, for example, for injecting fluid into the dermis or extracting fluid from tissue.

The term "transdermally" and variations thereof, is generally used to refer to any type of delivery of an active ingredient that crosses any portion of skin. That is, transdermally can generally include systemic delivery (i.e., where the active ingredient is transported across, or substantially through, the dermis such that the active ingredient is delivered into the bloodstream), as well as intradermal delivery (i.e., where the active ingredient is transported partially through the dermis, e.g., across the outer layer (stratum corneum) of the skin, where the active ingredient is delivered into the skin, e.g., for treating psoriasis or for local anesthetic delivery). That is, transdermal delivery as used herein includes delivery of an active ingredient that is transported across at least a portion of skin (but not necessarily all of the layers of skin), rather than merely being topically applied to an outer layer of the skin.

The phrase "hollow microneedle" refers to a specific microscopic structure that is designed for piercing the stratum corneum to facilitate the delivery of drugs through the skin. By way of example, microneedles can include needle or needle-like structures, as well as other structures capable of piercing the stratum corneum and delivering liquid drug formulations to skin or tissue layers beneath the stratum corneum.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a microneedle can be interpreted to mean "one or more" microneedles.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF DRAWINGS

The present invention will be further explained with reference to the drawing figures listed below, where like structure is referenced by like numerals throughout the several views.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to articles comprising hollow microneedles having a tip portion that penetrates skin and provides an opening through which a composition (e.g., a pharmaceutically-active compound) can be delivered into the skin tissue and other tissue disposed in or underlying the skin tissue. In particular, the present disclosure relates to certain aspects of the tip portion that can provide more-efficient delivery of compositions into the skin tissue. In addition, the aspects generally provide a more-robust method of manufacturing hollow microneedles and particularly provide a more-robust method of manufacturing high-aspect-ratio hollow microneedles.

Articles comprising hollow microneedles and/or hollow microneedle arrays are used, for example, to deliver compositions (e.g., compositions comprising active ingredients). Such articles are described, for example, in U.S. Pat. Nos. 8,088,321 and 8,246,893; and U.S. Patent Application Publication Nos. US2011/0213335, US2012/0123387, US2012/0041337; and International Patent Publication No. WO2012/074576, which are all incorporated herein by reference in their entirety.

Figure 1:
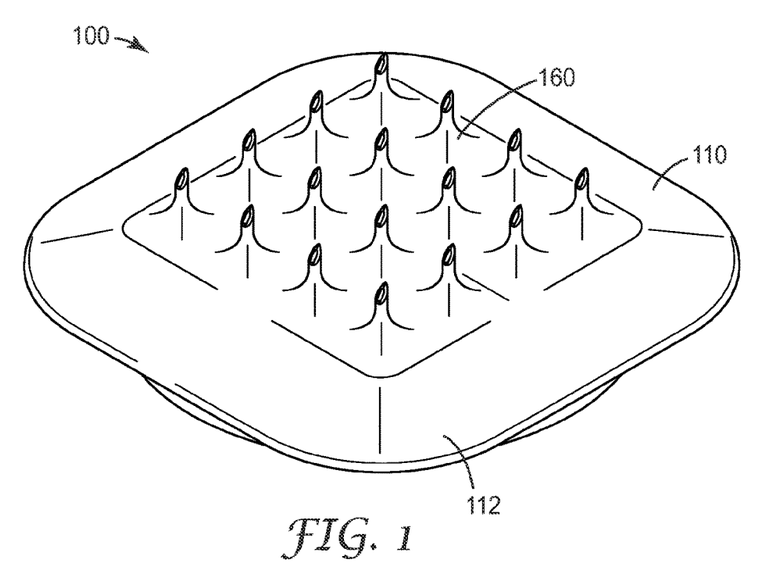
FIG. 1 is a perspective view of an embodiment of an article comprising a hollow microneedle.

Turning to the drawings, FIG. 1 shows one embodiment of an article 100 comprising at least one microneedle 160. In the illustrated embodiment, the article 100 comprises a square-shaped array of a plurality of microneedles 160. The article 100 comprises a unitary substrate 110 having a first side 112 from which the microneedles 160 extend. In any embodiment, an article according to the present disclosure can comprise a plurality of hollow microneedles. In any embodiment, the hollow microneedles can be arranged in an array (e.g., a regular array). Non-limiting examples of articles comprising hollow microneedles are described in PCT Publication Nos. WO2015/009531 and WO2015/009530, which are both incorporated herein by reference in their entirety.

Figure 2:
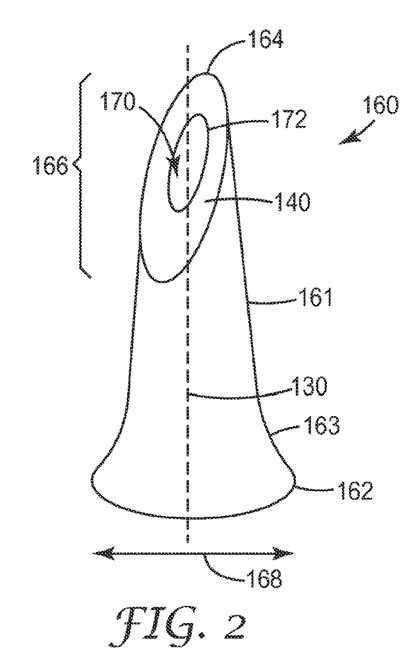
FIG. 2 is a perspective view of an embodiment of a hollow microneedle comprising a bevel face having an opening.

FIG. 2 shows one embodiment of a hollow microneedle 160. The microneedle 160 comprises an elongated body 161 having at least one major surface 163, central axis 130, a body diameter 168, a base 162 at one end of the body 161, and a tip portion 166 at the other end of the body 161. The body 161 can take the form of a variety of shapes including, but not limited to, cylindrical, conical, crateriform, pyramidal, and combinations thereof. The tip portion 166 comprises a bevel face 140 that extends diagonally, relative to the central axis, through the body 161 and thereby forming the tip 164. As used herein, the "tip" of a microneedle is a point of the microneedle that is farthest (as measured along the central axis) from the base of the microneedle. Preferably, the angle of the bevel face 140 with respect to the central axis 130 is sufficiently acute such that it forms a sharp edge (e.g., for penetrating skin) at the tip 164. The microneedle 160 further comprises a hollow channel 170 that extends from the tip portion 166 into the body 161 via a bevel opening 172 on the bevel face 140. Although illustrated as a relatively flat plane that is not coplanar with the at least one major surface of the microneedle, it is contemplated that, in any embodiment, the bevel face in which the bevel opening is disposed may be coplanar with the at least one major surface of the microneedle (not shown).

Figure 3:
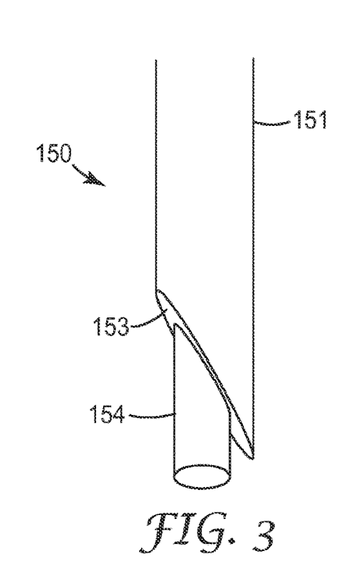
FIG. 3 is a perspective view of a mold part used to form a tip portion of the hollow microneedle of FIG. 2.
Figure 4:
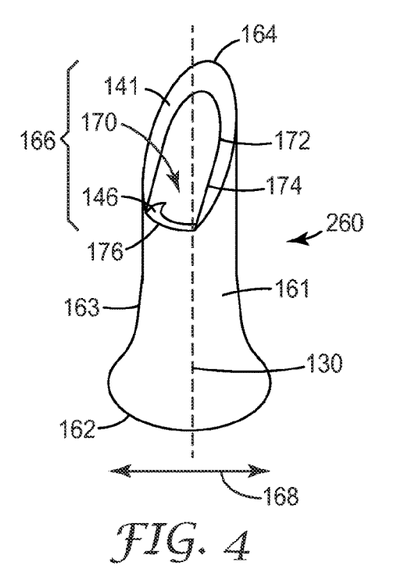
FIG. 4 is a perspective view of one embodiment of hollow microneedle having a bevel face with an opening according to the present disclosure.

FIG. 3 shows a perspective view of one embodiment of a mold part 150, referenced in the Examples as a "first mold section of the "first mold half", which is used to form the tip portion 166 of the hollow microneedle 160 of FIG. 2. The mold part 150 comprises a base 151. In the illustrated embodiment of FIG. 3, the base is cylindrical. The mold part further comprises a bevel-forming surface 153 and an extension 154. The bevel-forming surface 153 defines the shape and angle of the bevel face of the microneedle. The extension 154 defines the shape (e.g., circular) and size of the opening in the bevel face and also defines the shape (e.g., cylindrical) and diameter of the hollow channel in the microneedle. In any embodiment, the microneedle may comprise a hollow channel that extends only partially through the body of the microneedle (i.e., the hollow channel is a dead-end channel). In these embodiments, the extension 154 may also define the depth of the hollow channel that is made using the mold part 150.

FIGS. 4-8 show various views of one embodiment of a microneedle 260 according to the present disclosure. Similar to the microneedle 160 shown in FIG. 2, the microneedle 260 comprises an elongated body 161 having at least one major surface 163, central axis 130, a body diameter 168, a base 162 at one end of the body 161, and a tip portion 166 at the other end of the body 161. The body 161 can take the form of a variety of shapes including, but not limited to, cylindrical, conical, crateriform, pyramidal, and combinations thereof.

In contrast to the microneedle 160 of FIG. 2, the tip portion 166 of the microneedle 260 comprises a first bevel face 140 and a second bevel face 146. The first bevel face 140 is oriented diagonally with respect to the central axis 130 and extends through at least about 75% of the body diameter, the body diameter being measured along a plane that is perpendicular to the central axis at the point where the first bevel face is closest the base 162 relative to the central axis 130 (i.e., the body diameter at the second bevel face 146). In any embodiment, the first bevel face extends through about 75% to about 95% of the body diameter, the body diameter being measured along a plane that is perpendicular to the central axis at the point where the first bevel face is closest the base 162 relative to the central axis 130. In any embodiment, the first bevel face extends through at least about 80% of the body diameter, the body diameter being measured along a plane that is perpendicular to the central axis at the point where the first bevel face is closest the base 162 relative to the central axis 130. In any embodiment, the first bevel face extends through at least about 85% of the body diameter, the body diameter being measured along a plane that is perpendicular to the central axis at the point where the first bevel face is closest the base 162 relative to the central axis 130. In any embodiment, the first bevel face extends through at least about 90% of the body diameter, the body diameter being measured along a plane that is perpendicular to the central axis at the point where the first bevel face is closest the base 162 relative to the central axis 130. In any embodiment, the first bevel face extends through not more than about 95% of the body diameter, the body diameter being measured along a plane that is perpendicular to the central axis at the point where the first bevel face is closest the base 162 relative to the central axis 130. In any embodiment, the first bevel face extends through at least about 80% to about 95% of the body diameter, the body diameter being measured along a plane that is perpendicular to the central axis at the point where the first bevel face is closest the base 162 relative to the central axis 130.

Thus, in any embodiment, the second bevel face 146 extends through about 5% to about 25% of the body diameter of the microneedle.

Preferably, the pitch (i.e., angle) angle of the primary bevel (e.g., bevel face 140 of FIGS. 5 and 11A and dihedral-shaped primary bevel face 141 of FIG. 10A) with respect to the central axis 130 is sufficiently acute such that it forms a sharp edge (e.g., for penetrating skin) at the tip 164. In any embodiment, the pitch of the primary bevel is about 15° to about 40°, relative to the central axis 130. In a preferred embodiment, the primary bevel has a pitch of about 20° to about 35°, relative to the central axis 130. In a more preferred embodiment, the primary bevel has a pitch of about 25° to about 33°, relative to the central axis 130. In the illustrated embodiment of FIGS. 4-8, the tip 164 of the microneedle 260 is located at a point where the first bevel face 140 is farthest from the base 162 relative to the central axis.

Figure 10A:
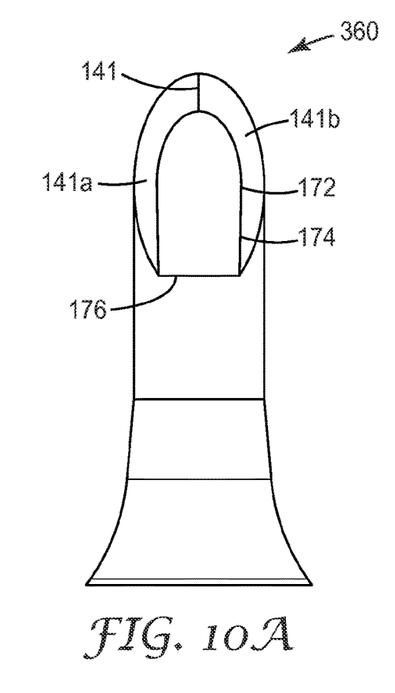
FIG. 10A is a side view, showing the bevel face and bevel opening, of another embodiment of a hollow microneedle according to the present disclosure.
Figure 10B:
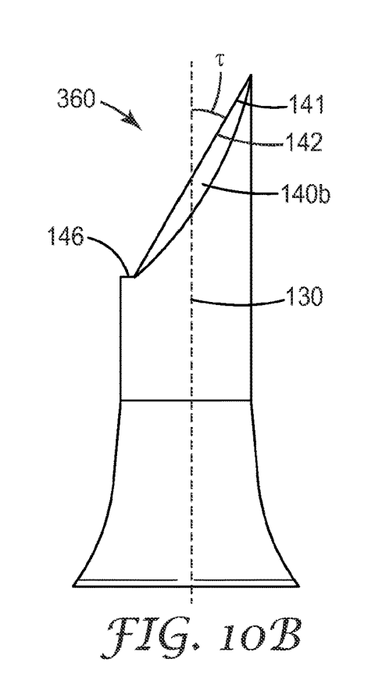
FIG. 10B is a side view of the hollow microneedle of FIG. 10A, showing one plane of the bevel face.

The microneedle 360 of the illustrated embodiment of FIGS. 10A-10B forms the shape of a triple bevel hypodermic needle. That is, it has a primary bevel face 141 with a first pitch (shown in FIG. 10B) relative to the central axis 130 and it has two secondary bevels 141a and 141b that have a second pitch relative to the primary bevel face 141. In any embodiment, the second pitch can be about 15° to about 40°, relative to the primary bevel. In any embodiment, the second pitch can be about 20° to about 30°, relative to the primary bevel.

Figure 6:
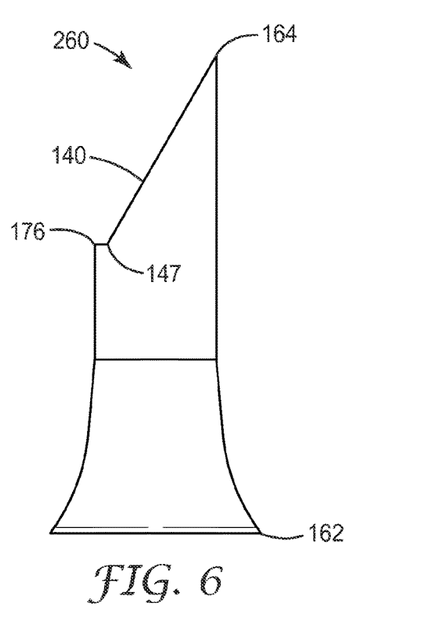
FIG. 6 is a side view of the hollow microneedle of FIG. 4.
Figure 7:
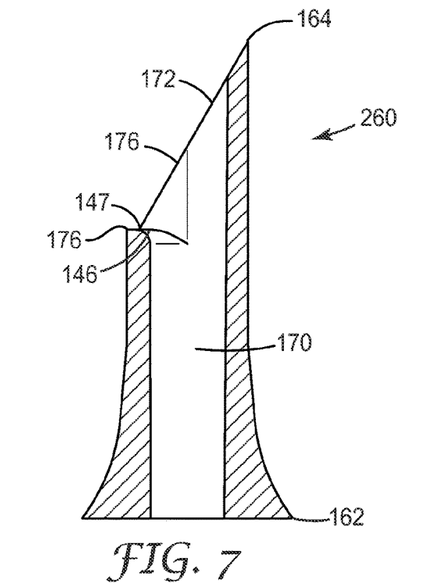
FIG. 7 is a cross-sectional view of the hollow microneedle of FIG. 5 taken along line 7-7.
Figure 8:
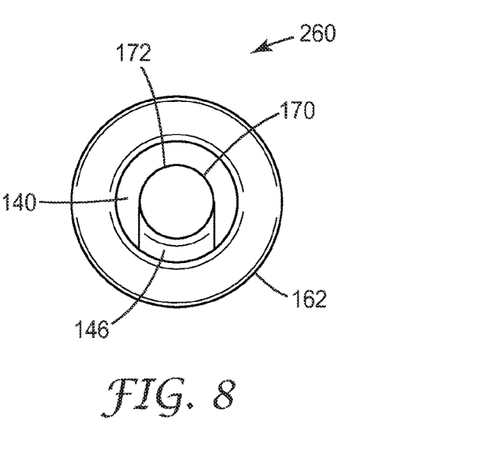
FIG. 8 is a top view of the hollow microneedle of FIG. 4.

The second bevel face 146 is oriented substantially perpendicular to the central axis and intersects the first bevel face along boundary 147 (see FIGS. 6 and 7). In any embodiment, the second bevel face 146 optionally may comprise a portion having a chamfer (i.e., a radius of curvature), as shown in FIG. 7.

Figure 5:
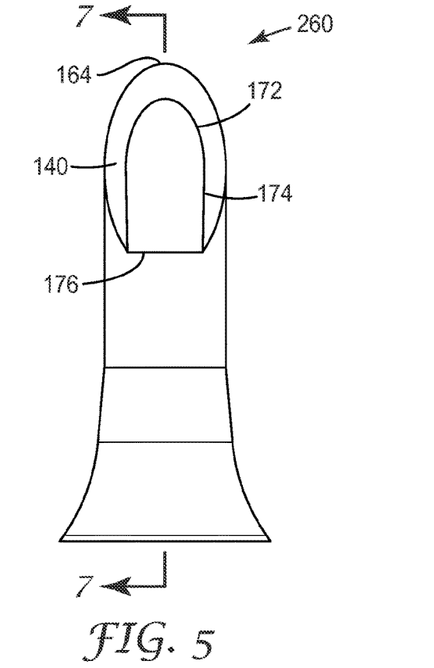
FIG. 5 is a side view of the hollow microneedle of FIG. 4, showing the bevel face and the opening.

The microneedle 260 further comprises a hollow channel 170 that extends axially into the body 161 from the tip portion 166 from a bevel opening 172. The bevel opening 172 is defined by a first edge 174 of the first bevel face 140 and a second edge 176 of the second bevel face 146. As shown in FIG. 5, the first bevel face 140 forms a surface in the shape of a partial ellipse that substantially surrounds the opening 172.

Figure 9:
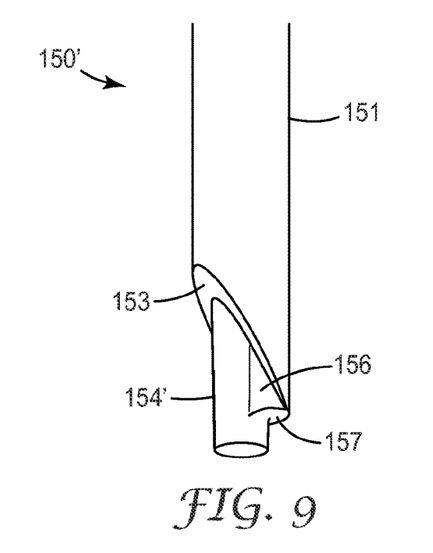
FIG. 9 is a perspective view of a mold part used to form a tip portion of the hollow microneedle of FIG. 4.

FIG. 9 shows a perspective view of one embodiment of a mold part 150', referenced in the Examples as a "first mold section" of the "first mold half", which is used to form the tip portion 166 of the hollow microneedle 260 of FIGS. 4-8. The mold part 150' comprises a base 151. Generally, cross-sectional shape of the base will match the exterior shape of the tip portion to be formed. In the illustrated embodiment of FIG. 9, the base is cylindrical.

The mold part 150' further comprises a bevel-forming surface 153 and an extension 154'. The bevel-forming surface 153 defines the shape and angle of the bevel face of the microneedle. The extension 154 defines the shape (e.g., circular) and size of the opening in the bevel face and also defines the shape (e.g., cylindrical) and diameter of the hollow channel in the microneedle. In any embodiment, the microneedle may comprise a hollow channel that extends only partially through the body of the microneedle (i.e., the hollow channel is a dead-end channel). In these embodiments, the extension 154' may also define the depth of the hollow channel that is made using the mold part 150. In any embodiment, an article according to the present disclosure may comprise hollow microneedles having a hollow channel that extends from one side of the article to another (e.g., to a reservoir located on the side opposite the microneedles, not shown).

In contrast to the mold part 150 of FIG. 3, the extension 154' of mold part 150' further comprises a protrusion 156 that increases the size of the opening that is created by the mold part 150'. The protrusion is truncated at rim 157, which defines the shape and location of the second bevel face formed in a process using the mold part 150'. In any embodiment, the rim 157 may be oriented substantially perpendicular to the central axis of the microneedle to be formed using the mold part 150'. In any embodiment, the rim 157 may comprise a radius of curvature.

In any embodiment, the first bevel face of a microneedle according to the present disclosure defines a plane. In any embodiment, the plane is a flat plane. In any embodiment, the plane may be curved or slightly curved. In any embodiment, the first bevel face may comprise a plurality of nonparallel planes. FIGS. 10A and 10B show one embodiment of a microneedle 360 comprising a primary bevel face 141 comprising a plurality of planes (e.g., planes formed by secondary bevels 141a and 141b, respectively). The planes intersect along third edge 142 defining the pitch of the primary bevel that extends from the opening 172 to the tip 164, forming a dihedral primary bevel face 141. Also shown in FIG. 10A are the first edge 174 and second edge 176 that form the opening 172 of the hollow microneedle 360. Also shown in FIG. 10B is the second bevel face 146, which intersects the planes formed by secondary bevels 141a and 141b of the primary bevel face 141.

Figure 11A:
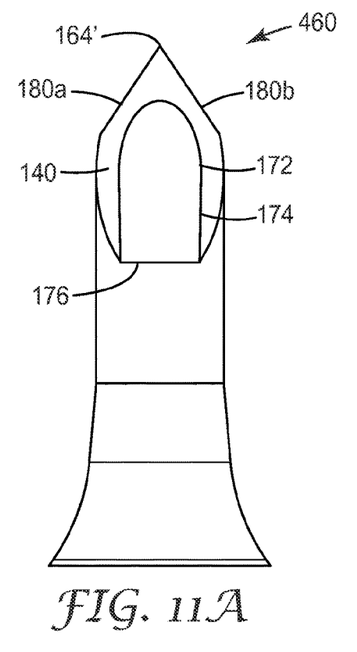
FIG. 11A is a side view, showing the bevel face and bevel opening, of yet another embodiment of a hollow microneedle according to the present disclosure.
Figure 11B:
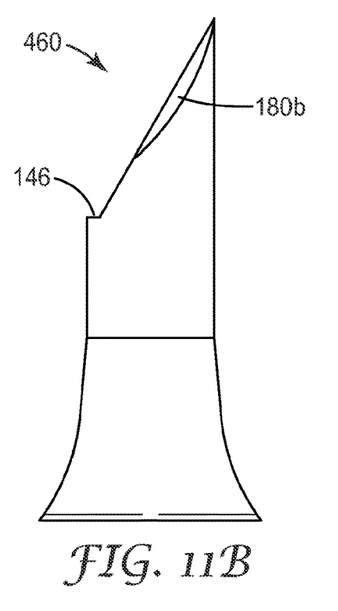
FIG. 11B is a side view of the hollow microneedle of FIG. 11A, showing one of the secondary bevels that forms the tip of the microneedle.

In any embodiment, a microneedle of the present disclosure optionally can comprise one or more auxiliary bevels that intersect the first bevel face. Typically, the auxiliary bevels are used to form a sharper tip for ease of penetration into and through skin tissue. FIGS. 11A and 11B show one embodiment of a microneedle 460 comprising a first bevel face 140 and two auxiliary bevels (bevels 180a and 180b) that intersect the first bevel face 140 to form a microneedle tip 164' with a sharp end. In any embodiment, the auxiliary bevel has a pitch (i.e., an angle in relation to the bevel face 140) of about 15° to about 40°. In a preferred embodiment, the bevel face 140 has a pitch of about 25° to about 35°. In a more preferred embodiment, the bevel face 140 has a pitch of about 30° 3 to about 35°. Also shown in FIG. 11A are the first edge 174 and second edge 176 that form the opening 172 of the hollow microneedle 460. Also shown in FIG. 11B is the second bevel face 146, which intersects the plane of secondary bevel 141b of the first bevel face 141.

Figure 12:
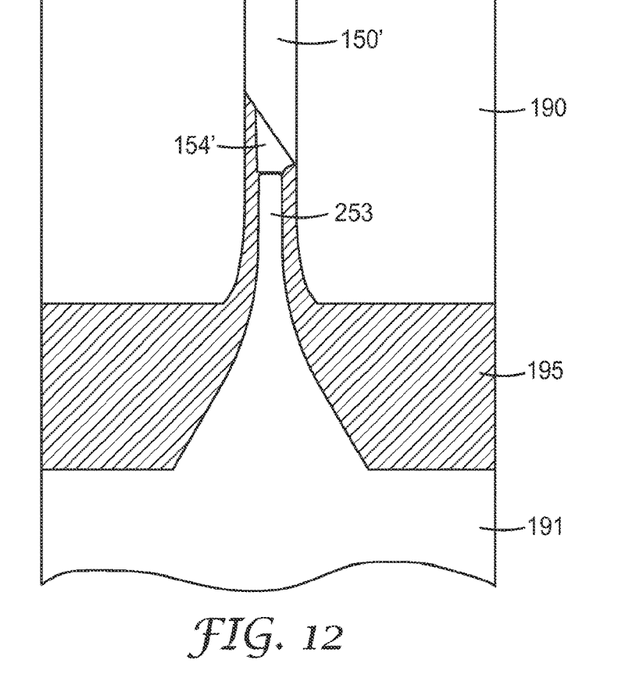
FIG. 12 is a schematic view of one embodiment of portions of mold parts that are used in a molding process to make an article with a hollow microneedle according to the present disclosure.

Hollow microneedles of the present disclosure can be made using molding processes that are known in the art. PCT Publication No. WO2014/099404, which is incorporated herein by reference in its entirety, for example describes the formation of microneedles using a molding process. FIG. 12 shows a schematic view of an apparatus for use in a molding process to make hollow microneedles of the present disclosure. As described in the Examples herein, a first mold half comprising a mold cavity part 190 and the mold part 150' of FIG. 9 is positioned proximate a second mold half 191, thereby creating a cavity 195 having the shape of the one or more microneedle and the article from which the microneedle projects (see FIG. 1, for example). The mold part 150' comprises the extension 154' that defines the opening and hollow channel proximate the tip of the formed microneedle. Optionally, the second mold half 191 comprises a projection 253 that defines the size and shape of a hollow channel that extends completely through the formed article. As described in PCT Publication No. WO2014/099404, the microneedles may be formed in such a manner that a hollow channel extending completely through the body of the microneedle may be formed using processes (e.g., laser drilling) subsequent to the molding process.

In another aspect, the present disclosure provides a method of making an article comprising at least one hollow microneedle that comprises a body having a central axis, a body diameter, a base, a tip portion, and a hollow channel. The method comprises providing a first mold half comprising at least one cavity. The at least one cavity includes a cavity opening and a cavity surface having a first projection extending therefrom toward the cavity opening. The first projection defines a first segment of the hollow channel, the first segment extending into the body of the microneedle from the base. The first projection comprises a first longitudinal axis. The method further comprises providing a second mold half comprising at least one second projection extending therefrom. The at least one second projection defines a tip portion of the at least one microneedle and a second segment of the hollow channel, the second segment extending into the body of the microneedle from a bevel opening proximate the tip of the at least one microneedle. The at least one second projection comprises a second longitudinal axis. The second projection is shaped and dimensioned to define the tip portion, as described herein. The method further comprises contacting at least the first mold half or the second mold half with moldable material (e.g., polymeric material, thermoplastic polymeric material), inserting the at least one second projection into the cavity opening so that the first projection is substantially aligned with the second projection, and forming the article. In any embodiment, after forming the article, the second projection causes the tip portion of the at least one microneedle to comprise a tip, a first bevel face oriented diagonally with respect to the central axis and extending through about least 75% to about 95% of the body diameter, a second bevel face oriented substantially perpendicular to the central axis and intersecting the first bevel face, a bevel opening defined by a first edge of the first bevel face and a second edge of the second bevel face, and a hollow channel that extends axially into the body from the bevel opening. In any embodiment, the second projection is inserted into the at least one cavity before contacting at least the first mold half or the second mold half with the moldable material. Alternatively, in any embodiment, at least the first mold half or the second mold half is contacted with the moldable material before inserting the second projection into the at least one cavity.

In any of the above embodiments of the method, the at least one cavity has a cavity aspect ratio (cavity length to cavity base width) of at least 1.5 to 1. In any of the above embodiments of the method, the first mold half comprises a plurality of the at least one cavities, wherein the second mold half comprises a plurality of the at least one second projections, wherein the plurality of second projections is aligned to be inserted simultaneously into the plurality of cavities.

Microneedle articles that are made according to the present disclosure can have a variety of configurations and features, such as those described in the following patents and patent applications, the disclosures of which are incorporated herein by reference in their entirety. One embodiment for the microneedle articles includes the structures disclosed in U.S. Pat. No. 6,312,612 (Sherman et al.), which describes tapered structures having a hollow central channel. Yet still another embodiment for the microneedle array articles includes the structures disclosed in U.S. Pat. No. 6,379,324 (Garstein et al.), which describes hollow microneedles having at least one longitudinal blade at the top surface of the tip of the microneedle. A further embodiment for the microneedle array articles includes the structures disclosed in U.S. Patent Application Publication Nos. US2012/0123387 (Gonzalez et al.) and US2011/0213335 (Burton et al.), which both describe hollow microneedles. A still further embodiment for the microneedle array articles includes the structures disclosed in U.S. Pat. No. 6,558,361 (Yeshurun) and U.S. Pat. No. 7,648,484 (Yeshurun et al.), which both describe hollow microneedle arrays and methods of manufacturing thereof.

Various embodiments of features of microneedles that can be employed in the microneedle articles of the present disclosure are described in PCT Publication No. WO 2012/074576 (Duan et al.), which describes liquid crystalline polymer (LCP) microneedles; and PCT Publication No. WO 2012/122162 (Zhang et al.), which describes a variety of different types and compositions of microneedles that can be employed in the microneedles of the present disclosure.

Articles comprising hollow microneedles having features according to the present disclosure can be made, for example, by injection molding processes that are known in the art. In some embodiments, the microneedle material can be (or include) a metal, a ceramic material, or a polymeric material, preferably a medical grade polymeric material. The microneedle material can be (or include) silicon or a metal such as stainless steel, titanium, or nickel titanium alloy. Exemplary types of medical grade polymeric materials include polycarbonate, liquid crystalline polymer (LCP), polyether ether ketone (PEEK), cyclic olefin copolymer (COC), polybutylene terephthalate (PBT). Preferred types of medical grade polymeric materials include polycarbonate and LCP.

The microneedle articles of the present disclosure can be manufactured in any suitable way such as by injection molding, compression molding, metal injection molding, photolithography, stamping, or extrusion. In any embodiment, hollow microneedle arrays can be made by injection molding of a polymer such as medical grade polycarbonate or LCP, followed by laser drilling to form the channels of the hollow microneedles. Nonlimiting examples of molding processes for molding polymeric materials into solid microneedle articles can be found in U.S. Pat. No. 8,088,321 (Ferguson et al.) and U.S. Patent Application Publication Nos. 2012/0258284 (Rendon) and 2012/0041337 (Ferguson et al.), each of which is incorporated herein by reference in its entirety. A non-limiting example of a publication that discloses the formation of hollow channels in articles comprising microneedles is PCT Publication No. WO2014/105458, which is incorporated herein by reference in its entirety.

In some embodiments, the microneedle material can be (or include) a biodegradable polymeric material, preferably a medical grade biodegradable polymeric material. Exemplary types of medical grade biodegradable materials include polylactic acid (PLA), polyglycolic acid (PGA), PGA and PLA copolymer, polyester-amide polymer (PEA).

In some embodiments, the hollow microneedles can be a prepared from a dissolvable, degradable, or disintegradable material referred to herein as "dissolvable microneedles". A dissolvable, degradable, or disintegradable material is any solid material that dissolves, degrades, or disintegrates during use. In particular, a "dissolvable microneedle" dissolves, degrades, or disintegrates sufficiently in the tissue underlying the stratum corneum to allow a therapeutic agent to be released into the tissue. The therapeutic agent may be coated on or incorporated into a dissolvable microneedle. In some embodiments, the dissolvable material is selected from a carbohydrate or a sugar. In some embodiments, the dissolvable material is polyvinyl pyrrolidone (PVP). In some embodiments, the dissolvable material is selected from the group consisting of hyaluronic acid, carboxymethylcellulose, hydroxypropylmethylcellulose, methylcellulose, polyvinyl alcohol, sucrose, glucose, dextran, trehalose, maltodextrin, and a combination thereof.

In any embodiment, the hollow microneedles can be made from (or include) a combination of two or more of any of the above mentioned materials. For example, the tip of a microneedle may be a dissolvable material, while the remainder of the microneedle is a medical grade polymeric material.

A microneedle or the plurality of hollow microneedles in a microneedle-containing article of the present disclosure can have a variety of shapes that are capable of piercing the stratum corneum. In some of the embodiments, one or more of the plurality of microneedles can have a square pyramidal shape, triangular pyramidal shape, stepped pyramidal shape, conical shape, microblade shape, or the shape of a hypodermic needle. In any embodiment, one or more of the plurality of microneedles can have a square pyramidal shape. In any embodiment, one or more of the plurality of microneedles can have a triangular pyramidal shape. In any embodiment, one or more of the plurality of microneedles can have a stepped pyramidal shape. In any embodiment, one or more of the plurality of microneedles can have a conical shape. In any embodiment, one or more of the plurality of microneedles can have the shape of a hypodermic needle. In any embodiment, a microneedle array article may comprise an array of microneedles having a combination of any two or more of the foregoing microneedle shapes. The shape of any microneedle in the microneedle array article can be symmetric or asymmetric. The shape of any microneedle in the microneedle array article can be truncated (for example, the plurality of microneedles can have a truncated pyramid shape or truncated cone shape). In a preferred embodiment, each microneedle of the plurality of microneedles in a microneedle array article has a square pyramidal shape.

In any embodiment, each microneedle of the plurality of microneedles in a microneedle array article is a hollow microneedle (that is, the microneedle contains a hollow bore through the microneedle). The hollow bore can be from the base of the microneedle to the tip of the microneedle or the bore can be from the base of the microneedle to a position offset from the tip of the microneedle. In any embodiment, one or more of the plurality of hollow microneedles in a hollow microneedle array can have a conical shape, a cylindrical shape, a square pyramidal shape, a triangular pyramidal shape, or the shape of a hypodermic needle.

In any embodiment, one or more microneedle of the plurality of hollow microneedles in a hollow microneedle array article can have a conical shape; optionally, with a radius of curvature. In any embodiment, one or more microneedle of the plurality of hollow microneedles in a hollow microneedle array article can have a cylindrical shape. In any embodiment, one or more microneedle of the plurality of hollow microneedles in a hollow microneedle array article can have a segment having a square pyramidal shape. In any embodiment, one or more microneedle of the plurality of hollow microneedles in a hollow microneedle array article can have a segment having a triangular pyramidal shape. In any embodiment, one or more microneedle of the plurality of hollow microneedles in a hollow microneedle array article can have a segment having the shape of a hypodermic needle. In a preferred embodiment, each microneedle of the plurality of hollow microneedles in a hollow microneedle array article has a segment with the shape of a conventional hypodermic needle.

In any embodiment, an article comprising a hollow microneedle according to the present disclosure may comprise a plurality of the microneedles. The plurality of the microneedles optionally may form an array. In any embodiment, the article can comprise an array of about 3 to about 30, inclusive, of the hollow microneedles of the present disclosure. In a preferred embodiment, the article can comprise an array of about 8 to about 20, inclusive, of the hollow microneedles of the present disclosure. In a more-preferred embodiment, the article can comprise an array of 12, 16, or 18 of the hollow microneedles of the present disclosure.

In any embodiment of an article comprising a plurality of hollow microneedles according to the present disclosure, the overall height of each microneedle is about 400 µm to about 3000 µm. In any embodiment of an article comprising a plurality of hollow microneedles according to the present disclosure, the overall height of each microneedle is about 400 µm to about 2000 µm. In any embodiment of an article comprising a plurality of hollow microneedles according to the present disclosure, the overall height of each microneedle is about 750 µm to about 1600 µm.

In any embodiment of an article comprising a plurality of hollow microneedles according to the present disclosure, a hollow channel extending through each of the microneedles has a diameter, proximate the tip of the microneedle, of about 10 µm to about 200 µm. In any embodiment of an article comprising a plurality of hollow microneedles according to the present disclosure, a hollow channel extending through each of the microneedles has a diameter, proximate the tip of the microneedle, of about 10 µm to about 120 µm. In any embodiment of an article comprising a plurality of hollow microneedles according to the present disclosure, a hollow channel extending through each of the microneedles has a diameter, proximate the tip of the microneedle, of about 25 µm to about 75 µm.

In any embodiment of an article comprising a plurality of hollow microneedles according to the present disclosure, a hollow channel extending through each of the microneedles has a cross-sectional area of about 75 µm$^2$ to about 32,000 µm$^2$. In any embodiment of an article comprising a plurality of hollow microneedles according to the present disclosure, a hollow channel extending through each of the microneedles has a cross-sectional area of about 75 µm$^2$ to about 18,000 µm$^2$. In any embodiment of an article comprising a plurality of hollow microneedles according to the present disclosure, a hollow channel extending through each of the microneedles has a cross-sectional area of about 700 µm$^2$ to about 3,000 µm$^2$.

The hollow microneedle array articles of the present disclosure can be manufactured by injection molding of a polymer such as medical grade polycarbonate or LCP. Typically, these processes use molds to form the substrate with the microneedles extending therefrom.

Figure 13:
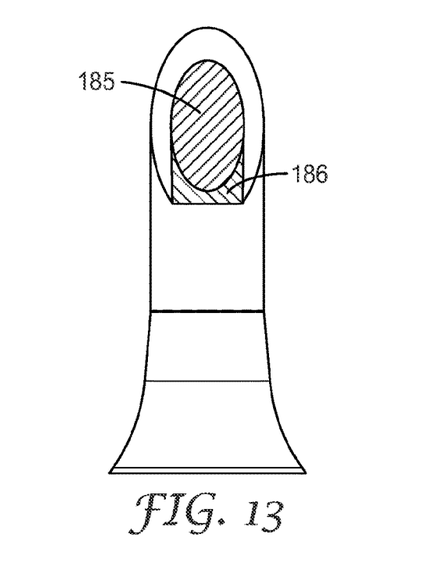
FIG. 13 is a duplication of FIG. 5, contrasting the area of a bevel opening in a traditional needle tip and the area of the bevel opening in a microneedle according to the present disclosure.

Microneedles of the present disclosure advantageously provide a larger opening, with respect to a predetermined microneedle wall thickness, than can be attained using conventional process known in the art. The larger opening facilitates the delivery of material (e.g., pharmaceutically-active compositions) from the hollow channel of the microneedle into the skin tissue and underlying layers of tissue. FIG. 13 shows the area 185 defined by a conventional opening in a hollow microneedle and the additional area 186 that is gained by making a microneedle according to the present disclosure.

In addition, using a process according to the present disclosure, the microscopic mold parts that are used to form the tip portion of the needle are significantly less susceptible to damage during extended use because the extensions that form the tip-proximal hollow channel in the microneedle are made stronger by the presence of the protrusion that forms the second bevel face.

Any of the above embodiments of a microneedle according to the present disclosure can be used for injecting fluid into a body. Any of the above embodiments of a microneedle according to the present disclosure can be used for extracting fluid from a body.

EXEMPLARY EMBODIMENTS

Embodiment A is an article, comprising:
at least one microneedle, the at least one microneedle comprising:
a base;
an elongated body having a central axis and a body diameter;
a tip portion comprising a tip, a first bevel face oriented diagonally with respect to the central axis and extending through about 75% to about 95% of the body diameter, a second bevel face oriented substantially perpendicular to the central axis and intersecting the first bevel face, a bevel opening defined by a first edge of the first bevel face and a second edge of the second bevel face; and
a hollow channel that extends axially into the body from the bevel opening;
wherein the second bevel face extends through no more than about 25% of the body diameter.

Embodiment B is the article of Embodiment A, wherein the at least one microneedle comprises a wall having a width at the second bevel face, wherein the second bevel face has a length, wherein the length of the second bevel face is equal to the width of the wall at the second bevel face.

Embodiment C is the article of Embodiment A or Embodiment B, wherein the first bevel face defines a plane.

Embodiment D is the article of Embodiment A or Embodiment B, wherein the first bevel face comprises a plurality of intersecting planes.

Embodiment E is the article of Embodiment D, wherein two or more of the planes intersect at a third edge, wherein the third edge extends along the first bevel face to the tip.

Embodiment F is the article of any one of the preceding Embodiments, wherein the first bevel face defines a partial ellipse that substantially surrounds the bevel opening.

Embodiment G is the article of any one of the preceding Embodiments, wherein a first two-dimensional area defined by the bevel opening is larger than a second two-dimensional area defined by a theoretical opening created by extending the first bevel face from the tip through 100% of the body diameter.

Embodiment H is the article of any one of Embodiments A through F, wherein the article further comprises a substrate having a first side and a second side, wherein the at least one microneedle extends from the first side of the substrate, wherein the channel extends from the opening through the elongated body to a second opening on the second side of the substrate.

Embodiment I is the article of any one of Embodiments A through H, wherein the at least one microneedle comprises a plurality of microneedles.

Embodiment J is a use of the article of any one of Embodiments A through I for injecting fluid into a body.

Embodiment K is a use of the article of any one of Embodiments A through I for extracting fluid from a body.

Embodiment L is a method of making an article comprising at least one hollow microneedle that comprises a body having a central axis, a body diameter, a base, a tip portion, and a hollow channel; the method comprising:
providing a first mold half comprising at least one cavity;
wherein the at least one cavity includes a cavity opening and a cavity surface having a first projection extending therefrom toward the cavity opening;
wherein the first projection defines a first segment of the hollow channel, the first segment extending into the body of the microneedle from the base;
wherein the first projection comprises a first longitudinal axis;
providing a second mold half comprising at least one second projection extending therefrom;
wherein the at least one second projection defines a tip portion of the at least one microneedle and a second segment of the hollow channel, the second segment extending into the body of the microneedle from a bevel opening proximate the tip of the at least one microneedle;
wherein the at least one second projection comprises a second longitudinal axis;
wherein the second projection is shaped and dimensioned to define the tip portion;
contacting at least the first mold half or the second mold half with moldable material;
inserting the at least one second projection into the cavity opening so that the first projection is substantially aligned with the second projection; and
forming the article;
wherein, the second projection causes the tip portion of the at least one microneedle to comprise a tip, a first bevel face oriented diagonally with respect to the central axis and extending through about 75% of the body diameter, a second bevel face oriented substantially perpendicular to the central axis and intersecting the first bevel face, a bevel opening defined by a first edge of the first bevel face and a second edge of the second bevel face, and a hollow channel that extends axially into the body from the bevel opening;
wherein, the second projection causes formation of the tip portion of the at least one microneedle such that the second bevel face extends through no more than about 25% of the body diameter.

Embodiment M is the method of Embodiment L, wherein the material comprises a metal, a ceramic material, or a polymeric material.

Embodiment N is the method of Embodiment L or Embodiment M, wherein the second projection is inserted into the at least one cavity before contacting at least the first mold half or the second mold half with the moldable material.

Embodiment O is the method of Embodiment L or Embodiment M, wherein at least the first mold half or the second mold half is contacted with the moldable material before inserting the second projection into the at least one cavity.

Embodiment P is the method of any one of Embodiments M through O, wherein the at least one cavity has a cavity aspect ratio (cavity length to cavity base width) of at least 1.5 to 1.

Embodiment Q is the method of any one of Embodiments M through O, wherein the first mold half comprises a plurality of the at least one cavities, wherein the second mold half comprises a plurality of the at least one second projections, wherein the plurality of second projections is aligned to be inserted simultaneously into the plurality of cavities.

EXAMPLES

Example 1. Fabrication of Microneedle Articles

The microneedle array articles were prepared from polymeric material using standard injection molding procedures. The molded microneedle array articles were prepared using a mold assembly prepared from three mold sections with each section machined from steel. The first mold section contained projections that defined the beveled shape of the needle tip in the molded article. Each projection in the first mold section had a further cylindrical extension that defined features of the tip segment of the microneedles tip, including the opening on a bevel proximate the tip of the microneedle and a portion of the hollow channel extending through the body of each microneedle. The second mold section served as a template to define the pattern of the microneedles in the molded article, the external shape and size of the microneedles in the molded article, and the first major surface of the molded article (including the peripheral portion). The third mold section contained cylindrical projections emerging from a planar surface with each projection defining a portion of the microneedle hollow channel and the opening located at the base of each microneedle in the molded article. The planar surface from which the projections emerged served to define the second major surface of the base segment of the molded article. The first and second mold sections were assembled to form a tight fit by inserting the projections of the first mold section into the corresponding openings in the second mold section. The assembled first and second mold sections formed the first mold half. The third mold section was used as the second mold half.

The first and second mold halves were installed in a mold base in a 60-ton injection molding press (Sodick Plustech LA 60, Sodick Plustech Co., Yokohama, Japan). As is common in the art, the parting line of the mold assembly had both primary and secondary vents for general air evacuation during injection of the polymeric material. Vectra MT1300 liquid crystal polymer (LCP) pellets (Ticona Engineering Polymers, Florence, Ky.) were loaded into a reciprocating screw and heated until molten. The first mold half and second mold half were heated to a temperature (hereafter referred to as the "mold temperature at injection") of 200° F. (93.3° C.). The molding cycle was initiated by closing the first mold half with the second mold half. The molds were clamped together with approximately 20 to 60 tons of force. In the clamped position, the projections of the second mold half did not contact any surface of the first mold half. A first portion (approx. 50-95% of the part size volume) of the total amount of material from the reciprocating screw was injected into the mold chamber at a fixed velocity (hereafter referred to as the "injection velocity") of 7 inches/second (17.8 cm/second). After injecting the first portion of material, the process was switched from an injection-driven to a pressure-driven mode by applying a fixed pressure (hereafter referred to as the "pack pressure") of 13,500 psi (93,079 kilopascal) to force the remainder of the molten material into the negative mold insert. The pack pressure was applied for a fixed time (hereafter referred to as the "hold time") of 5 seconds. The pack pressure was subsequently released and the mold chamber was cooled to an ejection temperature set below the softening temperature of LCP. The mold chamber was opened and the microneedle array article was ejected.

Example 2. Injection Apparatus Used to Test the Microneedle Articles

Fully assembled microneedle article injection apparatuses similar to apparatuses described in U.S. Patent Application Publication No. US2012/0123387 (FIGS. 1-13) and PCT Publication No. WO2014/099404 (FIGS. 2, 14 and 15) were used. The drug cartridge in each apparatus contained a 1 mL solution of 0.005% methylene blue in five percent aqueous dextrose. The injection apparatus from Example 2 of PCT Publication No. WO2014/099404 was used with the following exceptions. First, the section of the apparatus joined to the adhesive assembly was not milled to remove material. Second, the construction of the adhesive assembly was different. Instead of using the four layer adhesive of PCT Publication No. WO2014/099404, the adhesive assembly used was a laminate composed of only two layers. The first layer was a 0.10 mm thick sheet of 3M 1510 double sided tape (available from the 3M Company). The second layer was a 0.07 mm sheet of 3M 1524 transfer adhesive. The two layer adhesive assembly was positioned to cover the first major surface of base member of the lower housing at the rounded end section of the device. The adhesive assembly laminate was laser cut so that the size and shape of the adhesive assembly was matched to that of the device. The two layers of the adhesive assembly each contained cut-out regions that were aligned to each other and exactly matched the opening in the device housing. The device and adhesive assembly were oriented so that the first layer of the adhesive assembly was adhered to the lower housing of the device. The adhesive assembly was aligned with the device so that the opening in the first layer of the adhesive assembly was coincident with the opening in the device. A release liner was used during storage of the device to protect the exposed adhesive of the fourth layer of the adhesive assembly.

The hollow microneedle array article (as shown in FIG. 1) used in the injection apparatus was injection molded (as described in Example 1) from Vectra MT1300 liquid crystal polymer (LCP) in the shape of a square approximately 1.6 $cm^2$ in area. The article featured 12 hollow microneedles centered on the article and arranged along the perimeter of a square pattern. The microneedles extended from the first major surface of the article. The microneedles were evenly spaced with 4 microneedles defining each side of the square. The peripheral portion surrounding the square microneedle pattern canted away from the perimeter of the pattern with an 18 degree slope. The spacing between neighboring microneedles was about 2 mm (as measured from tip to tip). The microneedles were oriented so that the openings in the tip segments were all aligned and facing toward one side of the square pattern. The external diameter of each microneedle at the base was about 2 mm. The flared base segment of each microneedle had a radius of curvature of about 0.7 mm. Each microneedle was in the shape of a triple bevel hypodermic needle (33.6 degree bevel with a split bevel of 20 degrees). The tip segment of each microneedle was shaped as shown in FIG. 10A. Each microneedle had a total height of about 1500 microns as measured from the base to the tip. The distance from the tip of each microneedle to the center of the opening near the tip was about 400 microns. The average diameter of the hollow channel created by molding was about 100 microns. In order to complete the hollow channel in each microneedle a section of material (about 50 microns) was removed using a laser drilling procedure (femtosecond) described in U.S. Provisional Patent Application No. 61/746,198. The diameter of the hollow channel of each microneedle in the laser drilled region was about 70 microns.

Example 3. Alternative Injection Apparatus

The same microneedle injection apparatus as described in Example 2 was used with the exception that the wire diameter of the U-shaped leaf-like insertion spring (i.e. first stored energy device as described in U.S. Patent Application Publication No. US2012/0123387 (FIGS. 1-13) and PCT Publication No. WO2014/099404 (FIGS. 2, 14 and 15) was 1.40 mm instead of 1.50 mm.

Example 4. Alternative Injection Apparatus

The same microneedle injection apparatus as described in Example 2 was constructed with the exception that a different hollow microneedle array article was used. The hollow microneedle article was injection molded (as described in Example 1) from Vectra MT1300 liquid crystal polymer (LCP) in the shape of a square approximately 1.6 cm$^2$ in area. The microneedles extended from the first major surface of the article. The article featured 16 hollow microneedles evenly spaced and defining a 4 by 4 square pattern centered on the article. The peripheral portion surrounding the square microneedle pattern was canted away from the perimeter of the central portion with an 18 degree slope relative to a plane formed by the central portion. The spacing between neighboring microneedles was about 2 mm (as measured from tip to tip). The microneedles were oriented so that the openings in the tip segments were all aligned and facing toward one side of the square pattern. The external diameter of each microneedle at the base was about 2 mm. The flared base segment of each microneedle had a radius of curvature of about 0.7 mm. Each microneedle was in the shape of a triple bevel hypodermic needle (33.6 degree bevel with a split bevel of 20 degrees). The tip segment of each microneedle was shaped as shown in FIG. 10A. Each microneedle had a total height of about 1500 microns as measured from the base to the tip. The distance from the tip of each microneedle to the center of the opening near the tip was about 400 microns. The average diameter of the hollow channel created by molding was about 100 microns. In order to complete the hollow channel in each microneedle a section of material (about 50 microns) was removed using a laser drilling procedure (femtosecond) described in U.S. Provisional Patent Application No. 61/746,198. The diameter of the hollow channel of each microneedle in the laser drilled region was about 70 microns.

Example 5. Use of Microneedle Article to Inject a Substance

The study was conducted using Yorkshire cross domestic pigs (Midwest Research Swine, Gibbon, Minn.) in vivo. A soft region of the belly having minimal muscle content was selected as the application site for microneedle insertion. The application site was first trimmed with an electric clipper and then shaved using a razor and shaving cream. The shaved area was scrubbed using soapy water and a BUF-PUF exfoliation sponge (3M Company, St. Paul, Minn.) and then rinsed with deionized water. The animal was placed in a lateral recumbent position on a heated table (38° C.). The animal was anesthetized with isofluorene gas and maintained under anesthesia throughout the experiment. The application site was then wiped with a 70% isopropanol in water solution.

The injection apparatus of Example 3 was used. The release liner was removed from the adhesive assembly and the apparatus was adhered to the skin of the pig. During attachment of the device to the pig, the skin at the application site was gently stretched to provide a slight tension to the skin. The skin was then allowed to relax and the push-button was depressed to cause release of the applicator element and insertion of the microneedle array article into the skin of the pig. Removal of the tapered pin from the housing released the coiled spring which initiated the injection of the methylene blue solution into the pig. After completion of the injection, the apparatus was maintained on the skin for one additional minute. The apparatus was removed from the skin and the skin surface was examined to determine if there was any methylene blue solution on the surface of the skin. The presence of methylene blue solution on the skin was an indication that not all of the methylene blue was injected into the animal. The injection site was wiped with a pre-tared absorbent wipe and the wipe was then weighed to determine the amount of methylene blue that was not successfully delivered.

A total of three replicates were conducted. The injection times ranged from 54 to 73 seconds with the average injection time being 62 seconds. One of the apparatuses successfully delivered the methylene blue solution without any "leakage" (i.e. no methylene blue solution was observed on the skin surface). The other two apparatuses successfully delivered 91% and 98% of the methylene blue solution, respectively.

Example 6. Use of Microneedle Article

A study was conducted to determine the depth of penetration (DOP) of the microneedles of the array when applied to the skin surface of a Yorkshire cross domestic pigs (Midwest Research Swine), in vivo. The hollow microneedle array article described in Example 4 was used.

The microneedles on the article were coated using a three step process. The first two steps involved applying primer coatings to the microneedles and the third step involved applying a thin coating of Rhodamine B to the microneedles. In Step 1, the array articles were flood coated with a 35 microliter solution containing 0.5 mg/mL polyvinyl alcohol (80% hydrolyzed) (Sigma-Aldrich, Inc., St. Louis, Mo.) and 35 µg/ml of TWEEN® 80 (Sigma-Aldrich) in 90% (w/v) ethanol. The coated articles were then dried at 35° C. for 20 minutes. In Step 2, the articles from Step 1 were flood coated with 35 microliters of an aqueous solution of 33.3 mg/ml aluminum potassium sulfate (Penta Manufacturing, Livingston, N.J.). The coated articles were then dried at 35° C. for 30 minutes. In Step 3, the primed articles from Step 2 were flood coated with 40 microliters of an aqueous solution of 0.08% (w/v) Rhodamine B (Sigma-Aldrich). The coated articles were dried at 35° C. for 30 minutes. The three step process provided articles in which the microneedles were completely covered with a thin, opaque coating of Rhodamine B.

The ham region was selected as the application site for microneedle insertion. The application site was first trimmed with an electric clipper and then shaved using a razor and shaving cream. The shaved area was scrubbed using soapy water and a BUF-PUF exfoliation sponge (3M Company) and then rinsed with deionized water. The animal was placed in a lateral recumbent position on a heated table (38° C.). The animal was anesthetized with isofluorene gas and maintained under anesthesia throughout the experiment. The application site was then wiped with a 70% isopropanol in water solution.

The injection apparatus described in Example 4 with a Rhodamine B coated article was applied to the pig skin. The push-button was depressed to cause release the applicator element and insertion of the microneedles of the microneedle array into the skin of the pig. The applicator was maintained on the skin for an additional 5 minutes.

The applicator was removed from the animal. The depth of penetration (DOP) of the microneedles into the pig skin was determined indirectly by measuring the distance from the tip of the microneedle to where the Rhodamine B coating was wiped or dissolved from the microneedle after application into the skin. The measurement was conducted using a Nikon LV-100 microscope at 100× magnification (Nikon Instruments, Melville, N.Y.) with Image Pro® Plus digital image analysis software (Media Cybernetics, Bethesda, Md.). A total of two replicates were conducted. The mean microneedle DOP was determined by sampling all of the microneedles from each article (n=32). The results are presented in Table 1.

| | |
|---|---|
| Minimum DOP | 386 microns |
| Maximum DOP | 835 microns |
| Mean DOP (n = 32) | 595 microns |
| Standard Deviation | 119 microns |
| % RSD | 20% |

Example 7. Use of Microneedle Article

The procedure as described in Example 6 was used with the exception that the apparatus of Example 2 was used instead of the apparatus of Example 4. The results are presented in Table 2.

TABLE 2

Depth of Penetration DOP of Microneedles when Microneedle Article was Applied to the Ham Area (Example 7).

| | |
|---|---|
| Minimum DOP | 315 microns |
| Maximum DOP | 934 microns |
| Mean DOP (n = 24) | 736 microns |
| Standard Deviation | 125 microns |
| % RSD | 17% |

Example 8. Use of Microneedle Article to Inject a Substance

A study was conducted in human subjects (17 male, 23 female) to determine the time required to inject 1 mL of a 5% dextrose USP injection solution. The apparatus and hollow microneedle array article described in Example 2 was used with the exception that the drug cartridge was filled with the 5% dextrose USP injection solution instead of the methylene blue solution. The release liner was removed from the adhesive assembly and the apparatus was adhered to the thigh region of the subject. The push button was depressed to insert the microneedles into the skin of the subject. Next, the tapered pin was removed from the housing to release the coiled spring and begin the injection of the dextrose solution into the subject. The timer was started at the time of pin removal and stopped when the plunger was observed to reach the end of travel in the cartridge. The apparatus was removed from the subject and the skin surface around the application site was swabbed with a dry swab. The mass of the swab was measured immediately before and immediately after swabbing. The amount of residual fluid on the skin surface was determined by calculating the difference in the swab measurements. No attempt was made to differentiate between the different types of fluid (such as blood, interstitial fluid, or dextrose solution) found on the skin surface. The results are presented in Tables 3 and 4.

TABLE 3

| Injection Time | | |
|---|---|---|
| | Male Subjects | Female Subjects |
| Minimum Injection Time (sec) | 27 | 17 |
| Maximum Injection Time (sec) | 332 | 228 |
| Mean Injection Time (sec) | 110 | 67 |
| Standard Deviation (sec) | 86 | 57 |

TABLE 4

| Fluid Recovery | | |
|---|---|---|
| | Male Subjects | Female Subjects |
| Minimum Amount of Fluid at Site | 0 mg | 0 mg |
| Maximum Amount of Fluid at Site | 4 mg | 20 mg |
| Mean Amount of Fluid at Site | 2 mg | 2 mg |
| Standard Deviation | 3 mg | 4 mg |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:
1. An article, comprising:
at least one microneedle, the at least one microneedle comprising:
a base;
an elongated body having a central axis and a body diameter;
a tip portion comprising a tip, a first bevel face oriented diagonally with respect to the central axis and extending through about 75% to about 95% of the body diameter, a second bevel face oriented substantially perpendicular to the central axis and intersecting the first bevel face, a bevel opening defined by a first edge of the first bevel face and a second edge of the second bevel face; and
a hollow channel that extends axially into the body from the bevel opening;
wherein the second bevel face extends through no more than about 25% of the body diameter; and
wherein the first bevel face intersects the elongated body at the tip to form a sharp edge at the tip.
2. The article of claim 1, wherein the at least one microneedle comprises a wall having a width at the second bevel face, wherein the second bevel face has a length, wherein the length of the second bevel face is equal to the width of the wall at the second bevel face.

3. The article of claim 1, wherein the first bevel face defines a plane.

4. The article of claim 1, wherein the first bevel face comprises a plurality of intersecting planes.

5. The article of claim 4, wherein two or more of the planes intersect at a third edge, wherein the third edge extends along the first bevel face to the tip.

6. The article of claim 1, wherein the first bevel face defines a partial ellipse that substantially surrounds the bevel opening.

7. The article of claim 1, wherein a first two-dimensional area defined by the bevel opening is larger than a second two-dimensional area defined by a theoretical opening created by extending the first bevel face from the tip through 100% of the body diameter.

8. The article of claim 1, wherein the article further comprises a substrate having a first side and a second side, wherein the at least one microneedle extends from the first side of the substrate, wherein the channel extends from the opening through the elongated body to a second opening on the second side of the substrate.

9. The article of claim 1, wherein the at least one microneedle comprises a plurality of microneedles.

10. The article of claim 1, wherein the second bevel face is located closer to the base of the microneedle than the first bevel face.

11. A method of use of injecting fluid into a body, the method comprising providing an article of claim 1 that further comprises fluid, contacting the article with a body, and injecting the fluid into the body.

12. A method of extracting fluid from a body, the method comprising contacting an article of claim 1 with the body to puncture a surface of the body and removing fluid from the body through the hollow channel.

13. A method of making an article of claim 1, comprising at least one hollow microneedle that comprises a body having a central axis, a body diameter, a base, a tip portion, and a hollow channel; the method comprising:
providing a first mold half comprising at least one cavity;
wherein the at least one cavity includes a cavity opening and a cavity surface having a first projection extending therefrom toward the cavity opening;
wherein the first projection defines a first segment of the hollow channel, the first segment extending into the body of the microneedle from the base;
wherein the first projection comprises a first longitudinal axis;
providing a second mold half comprising at least one second projection extending therefrom;
wherein the at least one second projection defines a tip portion of the at least one microneedle and a second segment of the hollow channel, the second segment extending into the body of the microneedle from a bevel opening proximate the tip of the at least one microneedle;
wherein the at least one second projection comprises a second longitudinal axis;
wherein the second projection is shaped and dimensioned to define the tip portion;
contacting at least the first mold half or the second mold half with moldable material;
inserting the at least one second projection into the cavity opening so that the first projection is substantially aligned with the second projection; and
forming the article;
wherein, the second projection causes the tip portion of the at least one microneedle to comprise a tip, a first bevel face oriented diagonally with respect to the central axis and extending through about 75% to about 95% of the body diameter, a second bevel face oriented substantially perpendicular to the central axis and intersecting the first bevel face, a bevel opening defined by a first edge of the first bevel face and a second edge of the second bevel face, and a hollow channel that extends axially into the body from the bevel opening
wherein, the second projection causes formation of the tip portion of the at least one microneedle such that the second bevel face extends through no more than about 25% of the body diameter.

14. The method of claim 13, wherein the moldable material comprises a metal, a ceramic material, or a polymeric material.

15. The method of claim 13, wherein the second projection is inserted into the at least one cavity before contacting at least the first mold half or the second mold half with the moldable material.

16. The method of claim 13, wherein at least the first mold half or the second mold half is contacted with the moldable material before inserting the second projection into the at least one cavity.

17. The method of claim 13, wherein the at least one cavity has a cavity aspect ratio (cavity length to cavity base width) of at least 1.5 to 1.

18. The method of claim 13, wherein the first mold half comprises a plurality of the at least one cavities, wherein the second mold half comprises a plurality of the at least one second projections, wherein the plurality of second projections is aligned to be inserted simultaneously into the plurality of cavities.

* * * * *

UNITED STATES PATENT AND TRADEMARK OFFICE
CERTIFICATE OF CORRECTION

| | | |
|---|---|---|
| PATENT NO. | : 10,232,157 B2 | Page 1 of 1 |
| APPLICATION NO. | : 14/904975 | |
| DATED | : March 19, 2019 | |
| INVENTOR(S) | : Dennis G. Berry | |

It is certified that error appears in the above-identified patent and that said Letters Patent is hereby corrected as shown below:

On the Title Page

Abstract, Line 5, delete "The a" and insert -- The --, therefor.

In the Specification

Column 2,
Line 10, delete "microneedle" and insert -- microneedle. --, therefor.

In the Claims

Column 21,
Line 27, in Claim 11, delete "of use of" and insert -- of --, therefor.

Signed and Sealed this
Third Day of September, 2019

Andrei Iancu
*Director of the United States Patent and Trademark Office*